United States Patent
Zhang

(10) Patent No.: US 9,714,939 B1
(45) Date of Patent: Jul. 25, 2017

(54) CONCENTATED LIQUID SINGLE COMPONENT TMB SUBSTRATE FOR DETECTION ASSAY OF HORSERADISH PEROXIDASE

(71) Applicant: Hao Zhang, Vancouver (CA)

(72) Inventor: Hao Zhang, Vancouver (CA)

( * ) Notice: Subject to any disclaimer, the term of this patent is extended or adjusted under 35 U.S.C. 154(b) by 0 days.

(21) Appl. No.: 15/409,274

(22) Filed: Jan. 18, 2017

Related U.S. Application Data

(60) Provisional application No. 62/307,549, filed on Mar. 13, 2016.

(51) Int. Cl.
| | | |
|---|---|---|
| *G01N 33/58* | (2006.01) | |
| *G01N 33/535* | (2006.01) | |
| *C12Q 1/28* | (2006.01) | |
| *A61K 47/08* | (2006.01) | |
| *A61K 47/10* | (2017.01) | |
| *A61K 47/40* | (2006.01) | |

(52) U.S. Cl.
CPC ......... *G01N 33/535* (2013.01); *G01N 33/581* (2013.01); *A61K 47/08* (2013.01); *A61K 47/10* (2013.01); *A61K 47/40* (2013.01); *C12Q 1/28* (2013.01); *G01N 2333/908* (2013.01)

(58) Field of Classification Search
CPC ........ A61K 47/08; A61K 47/10; A61K 47/07; A61K 47/40; C12Q 1/28; G01N 33/581; G01N 33/535; G01N 2323/908; G01N 33/573

See application file for complete search history.

(56) References Cited

U.S. PATENT DOCUMENTS

| | | | | |
|---|---|---|---|---|
| 5,736,353 A | * | 4/1998 | Weavers | ............... C12N 9/0065 435/188 |
| 5,874,232 A | * | 2/1999 | Weavers | ............... C12N 9/0065 435/28 |

* cited by examiner

*Primary Examiner* — Shafiqul Haq

(57) ABSTRACT

Through special formulations, stable twenty-fold concentrate of single component TMB substrate is produced to minimize the volume and reduce the transportation cost. Reconstitution of the concentrate upon delivery to the distal site can be made with deionized water to yield single component TMB substrate solution for routine immunodiagnostic applications.

1 Claim, No Drawings

CONCENTATED LIQUID SINGLE COMPONENT TMB SUBSTRATE FOR DETECTION ASSAY OF HORSERADISH PEROXIDASE

This application claims the benefit of U.S. Provisional Application No. 62/307,549 filed on Mar. 13, 2016, entitled "Hao Zhang"

BACKGROUND OF INVENTION

The present invention relates to the concentrated forms of TMB substrate in the field of immunoassays by using horseradish peroxidase (HRP) for the enzyme labeling of detection antibodies. Preferably, single component TMB substrate is used for the signal detection during various forms of immunoassays. The stability and concentrated forms of such TMB substrate become desirable during the large scale practical applications in immunodiagnostics to facilitate the transportation to distal or remote sites.

SUMMARY OF INVENTION

The present invention relates to the formulations of single component TMB substrate in concentrated form to facilitate the distant transport of liquid substrate component in its concentrated form. The key production protocols required the formulations of TMB substrate in high concentration (20 fold concentrate or higher) with good solubility and stability. To achieve this goal, a protocol is disclosed have to ensure TMB solubility as stability under such concentration at room temperature for 24-36 months.

In the process of the present invention, the addition of polyhydroxy alcohol such as glycerol, and low molecular weight PEG would enhance the solubility of TMB in high concentrations. EDTA at specific PH provides protection of TMB oxidation by heavy transition metals. Notably, encasing of TMB with β-cyclodextrin in essential for the stability of TMB during the long term storage. This encasing process of TMB has been widely disclosed in several previous inventions. Thus in brief summary, the current invention involves the inclusion of special polyhydroxyl organic solvents to enhance the solubility of the encasing TMB in the final concentration forms for long term stability during storage and transport at room temperature.

DETAILS DESCRIPTION OF THE INVENTION

Abbreviated names of organic compounds.
DMSO—dimethyl sulfoxide
TMB—3,3',5,5' tetramethylbenzidine
BCD—β-cyclodextrin
PEG—polyethyle glycol of defined molecular weight (<2000)
EDTA—ethylediamine tetra-acetic acid
$H_2O_2$— hydrogen peroxide
HCl—Hydrochloric acid As noted, TMB has been widely accepted as an excellent peroxidase substrate. The mechanism of action in using TMB substrate during enzyme immunoassay with peroxidase has been well established for decades. Methods of preventing spontaneous oxidation of TMB and subsequent precipitation have been elucidated previously. This will lead to the storage shell life of TMB reagent to as long as 36 months or longer. Therefore, polyhydroxy alcohol has been shown to increase solubility of TMB or encased TMB in mixture of organic solvents and $H_2O$.

EXAMPLE 1

The Production of A twenty fold concentrated TMB Solution for ELISA Methods is described as follows: The reagents that are required to formulate twenty fold plus TMB concentrate are listed in the preferred weigh or final volume per 100 ml by the following table:

| Name | ml (g)/100 ml |
| --- | --- |
| a. Glycerol | 10 ml |
| b. PEG2000 | 10 g |
| c. DMSO | 10 ml |
| d. TMB | 1.3 g |
| e. BCD | 2 g |
| f. EDTA | 0.24 g |
| g. Citric Acid | 2 g |
| h. $H_2O_2$ | 0.22% |
| i. Isopropanol | 5 ml |
| j. Fumaric Acid | 1 g |
| k. Distill $H_2O$ | 70 ml |

Reagent Preparations Prior to Final Production of concentrate of one step TMB.
1. The resistance of deionized water should be greater than 18 megohm.
2. Preparation of BCD solution. 10 ml deionized water, 2 g, stirred until 2 g BCD is dissolved.
3. Additions of other chemicals are given as listed in the Table except for TMB and DMSO (sec 4.) and $H_2O_2$.
4. Prepare 1.3 g TMB in 40 ml DMSO with constant stirring
5. The final solution should consist of all the chemical reagents listed on the table with PH of the final solution adjusted to pH3.6+ or –0.02 with N HCl.
6. Deionized water was added until the final solution one step TMB concentrate to reach to 100 ml with 5-10 hours of constant stirring at 40-50° C. until all solid materials are fully dissolved.

I claim:
1. A 3,3',5,5'-tetramethylbezidine (TMB) 20-fold concentrate solution, said concentrate solution comprising 0.1 ml Glycerol, 0.1 g PEG2000, 0.1 ml DMSO, 0.013 g TMB, 0.02 g β-cyclodextrin (BCD), 0.0024 g EDTA, 0.02 g Citric Acid, 0.0022% $H_2O_2$, 0.05 ml Isopropanol, 0.01 g Fumaric acid, and 0.7 ml deionized water; wherein the final volume of the concentrate solution is 1 ml and the concentrate solution has a pH of about 3.6.

* * * * *